US009316652B2

(12) United States Patent
Joosten et al.

(10) Patent No.: US 9,316,652 B2
(45) Date of Patent: Apr. 19, 2016

(54) METHOD FOR DIAGNOSING LYME DISEASE USING A CELLULAR IMMUNOLOGICAL TEST

(75) Inventors: Leonardus Antonius Bernardus Joosten, Beuningen (NL); Mihai Gheorghe Netea, Nijmegen (NL); Johannes Willem Maarten van der Meer, Nijmegen (NL); Bart Julian Kullberg, Nijmegan (NL)

(73) Assignee: STICHTING KATHOLIEKE UNIVERSITEIT, Nijmegen (NL)

( * ) Notice: Subject to any disclaimer, the term of this patent is extended or adjusted under 35 U.S.C. 154(b) by 231 days.

(21) Appl. No.: 13/824,321

(22) PCT Filed: Sep. 21, 2011

(86) PCT No.: PCT/NL2011/050639
§ 371 (c)(1),
(2), (4) Date: May 31, 2013

(87) PCT Pub. No.: WO2012/039614
PCT Pub. Date: Mar. 29, 2012

(65) Prior Publication Data
US 2013/0296184 A1 Nov. 7, 2013

Related U.S. Application Data

(60) Provisional application No. 61/384,820, filed on Sep. 21, 2010.

(30) Foreign Application Priority Data

Sep. 21, 2010 (EP) .................................... 10178060

(51) Int. Cl.
*G01N 33/53* (2006.01)
*G01N 33/68* (2006.01)
*G01N 33/569* (2006.01)

(52) U.S. Cl.
CPC ...... *G01N 33/6866* (2013.01); *G01N 33/56911* (2013.01); *G01N 33/6869* (2013.01); *G01N 2333/20* (2013.01)

(58) Field of Classification Search
CPC ................................................. G01N 33/6866
See application file for complete search history.

(56) References Cited

FOREIGN PATENT DOCUMENTS

WO WO-94/19697 A1 9/1994

OTHER PUBLICATIONS

Aucott, John, et al., "Temporal Patterns of Early Cytokine Immune Response to Infection with Borellia Burdgorferi," American Journal of Tropical Medicine & Hygiene, 58th Annual Meeting of the American-Society-of-Tropical-Medicine-and Hygiene, Washington, D.C., Nov. 18, 2009, vol. 81, No. 5, Supplement S., p. 119 (Nov. 1, 2009).
Burgasova, O., et al., "Features of Cytokine Levels in Serum of Patients with Tick-Borne Borreliosis with Different Clinical Signs," Zurnal Mikrobiologii Epidemiologii I Immulnobiologii, Medicina, Moscow, RU, No. 3, pp. 67-71 (May 1, 2010).
Cepok, S., et al., The Immune Response at Onset and During Recovery from Borrelia Burgdorferi Meningoradiculitis, Archives of Neurology, American Medical Association, vol. 60, No. 6, pp. 849-855, (Jun. 1, 2003).
Ekerfelt, C., et al., "Augmented Intrathecal Secretion of Interferon-Gamma in Response to Borrelia Garinii in Neuroborreliosis," Journal of Neuroimmunology, Elsevier Science Publishers, vol. 89, No. 1-2, pp. 177-181 (Aug. 14, 1998).
Forsberg, P., et al., "The Outer Surface Proteins of Lyme Disease Borrelia Spirochestes Stimulate T Cells to Secrete Interferon-Gamma (IFM-γ): Diagnostic and Pathogenic Implications," Clinical & Experimental Immunology, vol. 101, No. 3, pp. 453-460 (1995).
International Search Report of PCT/NL2011/050639 dated Feb. 17, 2012.
Kisand, K., et al., "Propensity to Excessive Proinflammatory Response in Chronic Lyme Borreliosis," APMIS, Wiley Interscience, DK, vol. 115, No. 2, pp. 134-141, (Feb. 1, 2007).
Maduskuie, V.L., "Comparison of ELISA, Multiplex, and Microarray for Detection of Cytokines in Synovial Fluid," Abstracts of the General Meeting of the American Society for Microbiology on May 17-21, 2009, Philadelphia, PA, p. 1 (2009).
Murthy, P.K., et al., "Modulation of the Production of IL-12 and the Proinflammatory Cytokines IL-6, 1L-1-beta and TNF-Alpha by IL-10 in THP-1 Cells Stimulated with Borrelia Burgdorferi Antigens," Abstract of the General Meeting of the American Society for Microbiology, Washington, U.S., vol. 99, p. 258, (Jan. 1, 1999).
Pietruczuk, A., et al., "Serum Levels of Interleukin-18 (IL-18), Interleukin 1β (IL-1β), its Soluble Receptor sIL-1RII and C-reactive Protein (CRP) in Patients with Lyme Arthritis," Infection: A Journal of Infectious Disease, Urban & Vogel, vol. 34, No. 3, pp. 158-162 (Jun. 1, 2006).
Strauginger, R., et al., "Borrelia Burgdorferi Induces the Production and Release of Proinflammatory Cytokines in Canine Synovial Explant Cultures," Infection and Immunity, American Society for Microbiology, Washington, US, vol. 66, No. 1, pp. 247-258 (Jan. 1, 1998).
Author Not Known, Automation of ELISA and Strip Assays, Internet Citation, Nov. 21, 2014, XP007922907, Retrieved from the Internet: URL:http://www.bmgrp.com/fileadmin/user_upload/immunoassays/>Biomedica_Borrelia_ELISA_-_Info_Leaflet.pdf [retrieved on Feb. 13, 2015].
Godber, B. et al., Direct Quantification of Analyte Concentration by Resonant Acoustic Profiling, Clinical Chemistry 51:10:1962-1972 (2005).

*Primary Examiner* — Albert Navarro
(74) *Attorney, Agent, or Firm* — Choate, Hall & Stewart LLP

(57) ABSTRACT

The present invention relates to a method for diagnosing Lyme disease in a subject, the method comprising the steps of: (a) obtaining a sample from said subject, (b) contacting said sample with a source of *Borrelia* antigens and (c) determining the expression level of a pro-inflammatory cytokine in said sample at the end of step (b).

31 Claims, 2 Drawing Sheets

METHOD FOR DIAGNOSING LYME DISEASE USING A CELLULAR IMMUNOLOGICAL TEST

CROSS REFERENCE TO RELATED APPLICATIONS

The present application is the 35 U.S.C. 371 National Stage of International Application Number PCT/NL2011/050639, filed Sep. 21, 2011, which claims the benefit of U.S. Provisional Application No. 61/384,820, filed Sep. 21, 2010 and claims priority from European patent application EP10178060.9, filed Sep. 21, 2010, the contents of each of which are incorporated herein by reference.

SEQUENCE LISTING SUBMISSION VIA EFS-WEB

A computer readable text file, entitled "031902-5006-US-SEQ ST25.txt", created on or about Mar. 15, 2013, with a file size of about 31 KB contains the sequence listing for this application and is hereby incorporated by reference in its entirety.

FIELD OF THE INVENTION

The present invention relates to a method for diagnosing Lyme disease in a subject, using the determination of a pro-inflammatory cytokine expression level.

The present specification makes reference to a Sequence Listing (submitted electronically as a .txt file named "13824321_SeqList" on Feb. 17, 2015). The .txt file was generated on Feb. 11, 2015 and is 31,615 bytes in size. The entire contents of the Sequence Listing are incorporated herein by reference.

BACKGROUND OF THE INVENTION

Lyme disease or Lyme borreliosis is a vector-borne, multisystem inflammatory bacterial illness transmitted to humans by the bite of ticks (*Ixodes* species) carrying spirochetes of the genius *Borrelia*. The disease presentation varies widely, and may include rash and flu-like symptoms in its initial stage, and musculoskeletal, arthritic, neurologic, psychiatric and cardiac manifestations in later stages.

Lyme disease is clinically manifested in three phases as:
early localized disease with skin inflammation,
early disseminated disease (such as heart and nervous system involvement, including palsies and meningitis)
late disseminated disease (such as motor and sensory nerve damage and brain inflammation and arthritis).

Due to the difficulty in culturing the *Borrelia* spirochetes in the laboratory, diagnosis of Lyme disease is typically based on the clinical examination findings and a history of exposure to endemic Lyme areas. The laboratory tests most widely used are serological tests based on an Enzyme-linked immunosorbent assay (ELISA) test detecting antibodies to *Borrelia* species, mostly *B. burgdorferi*, *B. garinii* and *B. afzelii* (see for example WO 94/19697). This method is unfortunately characterized by a poor sensitivity and specificity, which sometimes provides false-positive results, and very often is not able to diagnose infected patients. Therefore, humoral immunological tests based on antibody detection are not a reliable basis for diagnosis of Lyme disease.

Western blot test may also be used to confirm positive results from an ELISA. The Western blot detects antibodies to several proteins of *Borrelia* species.

It is also possible to detect bacterial DNA in fluid drawn from an infected joint or other body sites using Polymerase chain reaction (PCR). This method is used for people who may have chronic Lyme arthritis. It may also be used to detect persistent infection in the cerebrospinal fluid of people who have nervous system symptoms. However, the sensitivity of PCR techniques is also low.

If diagnosed in the early stages, the disease can be cured with antibiotics. If left untreated, complications involving joints, the heart, and the nervous system can occur. It is therefore crucial to be able to specifically detect/diagnose Lyme disease in an early stage in order to avoid complications that may develop in later stages.

The significant disadvantages (poor sensitivity and specificity) of humoral immunity tests (ELISA and Western-blot) and PCR lead to a significant medical need for better diagnostic tests for diagnosing Lyme disease.

DESCRIPTION OF THE INVENTION

Diagnosis Method

Figure 1:
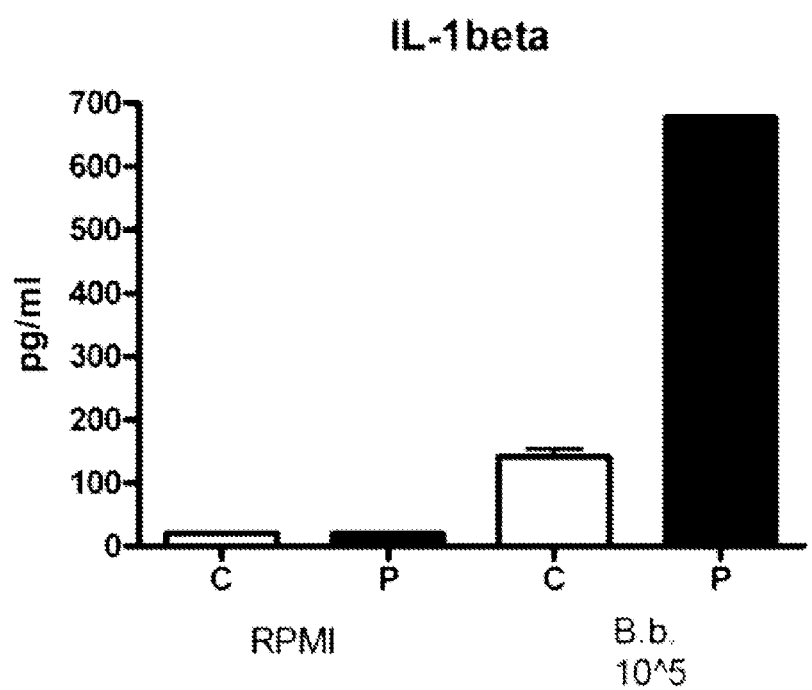
FIG. 1. Peripheral blood mononuclear cells (PBMC) were isolated from healthy volunteers (C) and patients with Lyme disease (P). $1.10^6$ cells/ml were stimulated for 24 h with *Borrelia* species ($1.10^5$/ml). Thereafter IL-1β was determined by ELISA.

In a first aspect, the invention relates to a method for diagnosing Lyme disease in a subject, the method comprising the steps of:
(a) obtaining a sample from said subject,
(b) contacting said sample with a source of *Borrelia* antigens and
(c) determining the expression level of a pro-inflammatory cytokine in said sample at the end of step (b).

In the context of the invention, "diagnosing Lyme disease" preferably means that a diagnosis is reached in at least the following cases presented below:

The Lyme disease may be diagnosed at an early stage before a classical test will diagnose it.

In this context "early stage" preferably means shortly after the clinical apparition of symptoms of local skin inflammation (EM) or before the stage wherein the disease has disseminated into the heart and/or nervous system or early disseminated into the heart and/or nervous system and/or before the stage of a disseminated disease involving featuring motor and sensory nerve damage and brain inflammation and arthritis also called a late disseminated disease involving featuring motor and sensory nerve damage and brain inflammation and arthritis as defined later herein.

Local skin inflammation is not always easily recognized or is not always easily recognizable (i.e. atypic EM) by the physician. The method of the invention could provide a specific diagnostic of the Lyme disease at an early stage in these cases. In this context "early stage" preferably means before the stage wherein the disease has disseminated into the heart and/or nervous system or early disseminated into the heart and/or nervous system and/or before the stage of a disseminated disease involving featuring motor and sensory nerve damage and brain inflammation and arthritis also called a late disseminated disease involving featuring motor and sensory nerve damage and brain inflammation and arthritis as defined later herein.

Alternatively some 20% or 30% of the Lyme patients will not develop EM. For these patients, the method of the invention also provides a specific diagnostic of the Lyme disease, preferably at an early stage preferably before the stage wherein the disease has disseminated into the heart and/or nervous system or early disseminated into the heart and/or nervous system and/or before the stage of a disseminated disease involving featuring motor and sensory nerve damage and brain inflammation and arthritis also called a late disseminated disease involving featuring motor and sensory nerve damage and brain inflammation and arthritis as defined later herein.

The disease may also be diagnosed using a method of the invention in a later stage in case the patient will consult a physician in a later stage. A later stage is preferably before the stage wherein the disease has disseminated into the heart and/or nervous system or early disseminated into the heart and/or nervous system and/or before the stage of a disseminated disease involving featuring motor and sensory nerve damage and brain inflammation and arthritis also called a late disseminated disease involving featuring motor and sensory nerve damage and brain inflammation and arthritis as defined later herein. In a later stage of the disease the method of the invention is also attractive compared to classical methods since at this later stage classical methods may not give a positive response or may give a positive response. However, classical methods often give false positive responses.

Alternatively, the disease may be diagnosed when the disease has disseminated into the heart and/or nervous system and/or at the stage of a disseminated disease involving nerve damage, brain inflammation, or arthritis also called a late disseminated disease involving nerve damage, brain inflammation, or arthritis and/or at the stage wherein the disease may become persistent or refractory to a 2 weeks antibiotic treatment. The clinical apparition of symptoms of local skin inflammation may be assessed by the physician. Local skin inflammation is usually characterized by an Erythema migrans (EM) that occurs at the site of the tick bite. The rash is usually salmon to red-colored; the color may cover the entire lesion or may have an area in the centre that is flesh-colored. In some cases, the rash consists of multiple rings, which give it a "bull's eye" appearance.

Preferably, the invention relates to a method for diagnosing Lyme disease shortly after the clinical apparition of symptoms of local skin inflammation (EM) in an subject, the method comprising the steps of:

(a) obtaining a sample from said subject,
(b) contacting said sample with a source of *Borrelia* antigens and
(c) determining the expression level of a pro-inflammatory cytokine in said sample at the end of step (b).

The assessment that the disease has already reached a stage wherein it has disseminated into the heart and/or nervous system may be assessed using serology, which has a poor sensitivity and specificity.

The assessment that the disease has already reached a disseminated stage with, among others, featuring motor and sensory nerve damage and brain inflammation and arthritis, also called a late disseminated stage with, among others, featuring motor and sensory nerve damage and brain inflammation and arthritis may be assessed using PCR to detect bacterial DNA in these organs/tissues. However, organ biopsies are very seldom available for testing in patients with chronic Lyme disease.

In this context, "shortly after the clinical apparition of symptoms of local skin inflammation (EM)" preferably means at least one day, at least two days, at least three days, at least four days, at least five days, at least six days, at least seven days, at least eight days, at least nine days, at least ten days at least 15 days, at least 20 days, at least 25 days, at least 30 days or more after the clinical apparition of symptoms of local skin inflammation.

In this context, "shortly after the clinical apparition of symptoms of local skin inflammation (EM)" preferably means before the stage wherein the disease has disseminated into the heart and/or nervous system or early disseminated into the heart and/or nervous system and/or before the stage of a disseminated disease involving featuring motor and sensory nerve damage and brain inflammation and arthritis also called a late disseminated disease involving featuring motor and sensory nerve damage and brain inflammation and arthritis. In this context, "before" preferably means at least one day, at least two days, at least three days, at least four days, at least five days, at least six days, at least seven days, at least eight days, at least nine days, at least ten days at least 15 days, at least 20 days, at least 25 days, at least 30 days or more before the stage wherein the disease has disseminated into the heart and/or nervous system or early disseminated into the heart and/or nervous system and/or before the stage of a disseminated disease involving featuring motor and sensory nerve damage and brain inflammation and arthritis also called a late disseminated disease involving featuring motor and sensory nerve damage and brain inflammation and arthritis.

In the context of the invention, diagnosis preferably means a predictive risk assessment of the subsequent development of Lyme disease in a subject.

In the context of the invention, a subject may be an animal or a human being. The diagnosis method may be applied as often as necessary in a subject. Preferably, a subject diagnosed is a subject suspected to have a high risk of having or developing chronic Lyme disease, due for example to the fact that this subject lives in a region wherein the Lyme disease is common, this subject spends a lot of time outdoors, including a subject who works outdoors, gardens, or participates in outdoor activities such as hunting or hiking or subject has a pet. Preferably, a subject is a human being. In a preferred method, the Lyme disease is diagnosed when step (c) leads to the finding of a detectable expression level or an increase of the expression level of a pro-inflammatory cytokine.

A pro-inflammatory cytokine is a cytokine that is able to promote systemic inflammation.

A pro-inflammatory cytokine is preferably selected from the group consisting of IL-1β, or IFNγ, IL-6, and IL-17. Good results were obtained using IL-1β. IL-1β is therefore a preferred pro-inflammatory cytokine in this context.

Optionally in a method of the invention, one may compare the expression level of a pro-inflammatory cytokine as determined in step (c) with a reference value for said expression level, the reference value preferably being the average value for said expression level in a control sample. In the context of the invention, "a reference value" for the expression level of a pro-inflammatory cytokine is preferably the average value for said expression level in a control sample. A control sample may be derived from a control subject or from control subjects or from the medium or culture medium used for step (b). A control subject may be a subject who do not live in a region at risk or who does not spend a lot of time outdoors. A pro-inflammatory cytokine tested may be not detectable in "a reference value". Said reference value may therefore be 0 or nor detectable in an assay as defined herein. In other words, said cytokine may not be detectable in a control sample.

The assessment of the expression level of the respective pro-inflammatory cytokine may be directly realised at the protein expression level (quantifying the amount of the cytokine), and/or indirectly by quantifying the amount of a nucleotide sequence encoding the respective cytokine (the value from a subject wherein the method is being carried out and optionally the reference value from a control sample). A nucleotide acid sequence encoding a human IL-1β, IFNγ, IL-6, IL-17 is given as SEQ ID NO:1, 2, 3, 4 respectively. A corresponding amino acid sequence of human IL-1β, IFNγ, IL-6, IL-17 is given as SEQ ID NO:5, 6, 7, 8 respectively. The skilled person will understand that it is possible to isolate multiple iso forms of each of the identified pro-inflammatory cytokine depending on the subject to be tested.

In a preferred embodiment, a pro-inflammatory cytokine to be quantified has:
  at least 60% (or at least 65%, at least 70%, at least 75%, at least 75%, at least 80%, at least 85%, at least 90%, at least 95%, at least 97%, at least 99% or more or 100%) identity or similarity with SEQ ID NO:5, 6, 7, or 8 and/or is encoded by a nucleotide acid sequence which has at least 60% (or at least 65%, at least 70%, at least 75%, at least 75%, at least 80%, at least 85%, at least 90%, at least 95%, at least 97%, at least 99% or more or 100%) identity or similarity with SEQ ID NO:1, 2, 3, or 4.

In another preferred embodiment, a nucleotide acid sequence encoding the respective pro-inflammatory cytokine to be quantified has:
  at least 60% (or at least 65%, at least 70%, at least 75%, at least 75%, at least 80%, at least 85%, at least 90%, at least 95%, at least 97%, at least 99% or more or 100%) identity or similarity with SEQ ID NO:1, 2, 3 or 4 and/or encodes an amino acid sequence of the pro-inflammatory cytokine (e.g. IL-1β, IFNγ, IL-6, IL-17) that has at least 60% (or at least 65%, at least 70%, at least 75%, at least 75%, at least 80%, at least 85%, at least 90%, at least 95%, at least 97%, at least 99% or more or 100%) identity or similarity with an amino acid sequence encoded by SEQ ID NO:1, 2, 3 or 4.

Identity and similarity are later herein defined. The quantification of the amount of a nucleotide sequence encoding a pro-inflammatory cytokine is preferably performed using classical molecular biology techniques such as (real time) PCR, arrays or northern analysis. In this embodiment, a nucleotide sequence encoding a pro-inflammatory cytokine means a messenger RNA (mRNA). Alternatively, according to another preferred embodiment, in a diagnosis method the expression level of a pro-inflammatory cytokine is determined directly by quantifying the amount of said pro-inflammatory cytokine Quantifying a polypeptide amount may be carried out by any known technique. Preferably, a polypeptide amount is quantified using a molecule which specifically binds to said pro-inflammatory cytokine Preferred binding molecules are selected from: an antibody, which has been specifically raised for recognizing said pro-inflammatory cytokine, any other molecule which is known to specifically bind said pro-inflammatory cytokine. Such antibody could be used in any immunoassay known to the skilled person such as western blotting, or ELISA (Enzyme-Linked Immuno Sorbent Assay) or FACS (Fluorescence Activated Cell Sorting) using latex beads. The preparation of an antibody is known to those skilled in the art. A short explanation of methods that could be used to prepare antibodies is later herein given. Suitable antibodies are commercially available. For example antibodies from R&D systems could be used to assess IL-1β, IL-6, IL-17 or IFNγ. Such antibodies could be used for assessing such cytokine by ELISA (duo-set). In the context of the invention, any other molecule known to bind the cytokine tested may be a nucleic acid, e.g. a DNA regulatory region, a polypeptide, a metabolite, a substrate, a regulatory element, a structural component, a chaperone (transport) molecule, a peptide mimetic, a non-peptide mimetic, or any other type of ligand. Mimetic is later herein defined. Examples of molecules known to bind a pro-inflammatory cytokine, include a receptor for said pro-inflammatory cytokine, an antibody directed against said pro-inflammatory cytokine. In case, IL-1β is chosen as a pro-inflammatory cytokine, a preferred anti-IL1β antibody is the IL-1F2 (from R&D systems) antibody. Binding of a pro-inflammatory cytokine to a second binding molecule may be detected by any standard methods known to those skilled in the art. Suitable methods include affinity chromatography co-electrophoresis (ACE) assays and ELISA. The skilled person will understand that alternatively or in combination with the quantification of a nucleic acid sequence encoding a pro-inflammatory cytokine tested and/or a corresponding polypeptide, the quantification of a substrate of a corresponding polypeptide or of any compound known to be associated with a function or activity of a corresponding polypeptide or the quantification of a function or activity of a corresponding polypeptide using a specific assay is encompassed within the scope of the diagnosis method of the invention. For example, trans-activation of a target gene of a pro-inflammatory cytokine or a molecule known to bind a pro-inflammatory cytokine can be determined and quantified, e.g., in a transient transfection assay in which the promoter of the target gene is linked to a reporter gene, e.g., P-galactosidase or luciferase. Such evaluations can be done in vitro or in vivo or ex vivo.

A method of the invention may encompass determining the expression level of at least one, or two or three or four pro-inflammatory cytokines in a sample at the end of step (b). For example IL-1β and IL-6 or IFNγ and IL-17 could be assessed. It is expected that IL-1β and IL-6 are produced within 48 hours of culture, whereas IFNγ and IL-17 are expected to be produced within 7 days of culture.

In a method of the invention, a sample from a subject is used. A method of the invention is therefore an in vitro or ex vivo method. A sample preferably comprises or consists of a fluid obtained from a subject. More preferably, a fluid comprises or consists of or is selected from: urine, blood, spinal cord fluid, saliva, semen, or bronchoalveolar lavage. A preferred fluid is, comprises, consists of or is derived from blood. Blood may be diluted before being further used. The dilution may be 1:4, 1:5 or 1:6. The dilution is preferably carried out in a medium, preferably a culture medium such as RPMI 1640 or a buffered solution.

In a method of the invention, said obtained sample of step (a) is subsequently contacted with a source of *Borrelia* antigens. The contacting step may have a duration of at least 1, 2, 3, 4, 5, 6, 7, 8 up to 24 hours, or longer. Preferably the contact has a duration of 4-96 hours. This contact step may be a culture step in a culture medium such as RPMI 1640. At least $10^4$ and up to $10^6$ bacteria may be inoculated at the start of the contacting step. Preferred species of *Borrelia* as a source of *Borrelia* antigens include: *B. burgdorferi*, more preferably the strain ATCC 35210, *B. garinii*, more preferably the strain ATCC 51383 and *B. afzelii*, more preferably the strain ATCC 51567. Therefore, in step (b) the *Borrelia* antigen is preferably from a species of *Borrelia* selected from: *B. burgdorferi*,

*B. garinii* and *B. afzelii*. These strains are preferred since they are the most widely present in Europe and in America.

A source of a *Borrelia* antigen may mean that a whole *Borrelia* cell or a *Borrelia* cell is being used. In a preferred embodiment, a whole *Borrelia* cell or a *Borrelia* cell is heat-inactivated or formalin fixated. Heat-inactivated could be replaced by heat-killed. The skilled person knows how to obtain heat-inactivated or formalin fixated *Borrelia* cells. Heat-inactivated cells are preferably prepared by heating at 52, 53, 54, 55 or 56 for 20, 25 or 30 minutes. More preferably heat-inactivated cells are prepared by heating at 52° C. for 30 minutes. Formalin fixated cells may be obtained by contacting the cells with formaldehyde for 40, 50, 60 minutes. More preferably, cells are contacted or transferred to 4% formaldehyde for one hour. Subsequently cells are washed several times with a saline buffer such as PBS (Phosphate Buffered Saline) buffer.

Alternatively, part of a *Borrelia* cell may be used. A part of a *Borrelia* cell is preferably an antigenic part thereof; it comprises or consists of an antigen. An antigen may be a protein, a digest of the protein and/or a fragment thereof, which may be in a purified form or may be comprised within a crude composition, preferably of biological origin, such as a lysate, sonicate or fixate of a *Borrelia*. Alternatively, an antigen may be chemically synthesized or enzymatically produced in vitro. The source of a protein, or fragment thereof as antigen, may also be a nucleic acid encoding said, or fragment thereof, from an RNA or DNA template. In a preferred embodiment, a source of a *Borrelia* antigen is a whole *Borrelia* cell or an antigen from said cell.

The use of a whole *Borrelia* cell is attractive and preferred above the use of a part of a cell for at least two reasons. The use of a whole cell is easier and cheaper for the skilled person. There is no need to identify and subsequently synthesize suitable parts (i.e. antigenic parts) of a cell. In addition, by using a whole cell, all potential suitable part (i.e. all antigens) of said cell are present. The diagnostic method is therefore expected to be far more sensitive and efficient than a corresponding diagnostic method carried out using a given antigen.

In a preferred method wherein in step (b) several species of *Borrelia* are used as a source of a *Borrelia* antigens, the sample of step (a) is divided into several sub-samples, each sub-sample being contacted with a source of antigens from one species of *Borrelia*. This preferred method may allow us to identify the *Borrelia* species that infected a given subject.

Subsequently, the expression level of a pro-inflammatory cytokine is determined in said sample at the end of step (b). First a nucleotide sequence encoding said pro-inflammatory cytokine and/or said pro-inflammatory cytokine are extracted and optionally purified using known methods to the skilled person. In a preferred embodiment, at the end of step (b), the supernatant is isolated by centrifugation. Centrifugation may be carried out at 1200 rpm and at 4° C. Alternatively, one may add a detergent to the sample at the end of step b). Several detergents could be used such as Triton X 0.1%. Adding a detergent is attractive since it is expected that no centrifugation step is needed. One may determine the expression level of a pro-inflammatory cytokine in the sample comprising said detergent, which is also called a cell lysate.

In a more preferred diagnostic method, Lyme disease is diagnosed when the expression of a pro-inflammatory cytokine is detectable or detected and optionally when the comparison leads to the finding of a detectable expression of said pro-inflammatory cytokine and/or an increase of the expression level of said pro-inflammatory cytokine. In control subjects and in control samples as defined before, pro-inflammatory cytokine expression is generally not detectable.

Detection of the expression of a pro-inflammatory cytokine or an increase of the expression level of said pro-inflammatory cytokine and/or an increase or a detection of the expression level of a nucleotide sequence encoding said pro-inflammatory cytokine (or steady state level of said pro-inflammatory cytokine) is preferably defined as being a detectable expression level or a detectable change of the expression level of said pro-inflammatory cytokine and/or of a nucleotide sequence encoding said pro-inflammatory cytokine (or steady state level of the encoded pro-inflammatory cytokine or any detectable activity of said pro-inflammatory cytokine or detectable change in a biological activity of said pro-inflammatory cytokine) using a method as defined earlier on as compared to the expression level of said pro-inflammatory cytokine and/or of a corresponding nucleotide sequence (or steady state level of the corresponding encoded pro-inflammatory cytokine) in a control subject or in a control. According to a preferred embodiment, detection or an increase of a pro-inflammatory cytokine activity is quantified using a specific mRNA assay for said pro-inflammatory cytokine gene as earlier defined herein. Preferably, an increase of the expression level of a nucleotide sequence encoding a pro-inflammatory cytokine means an increase of at least 5% of the expression level of said nucleotide sequence using PCR. Preferred primers used for the PCR are identified as SEQ ID NO:9 and SEQ ID NO:10 when a pro-inflammatory cytokine is IL-1β: forward CAGCTACGAATCTCCGACCAC and reverse GGCAGGGAACCAGCATCTTC. More preferably, an increase of the expression level of a nucleotide sequence means an increase of at least 10%, even more preferably at least 20%, at least 30%, at least 40%, at least 50%, at least 70%, at least 90%, at least 150%, or more.

Preferably, an increase of the expression level of a pro-inflammatory cytokine means an increase of at least 5% of the expression level of said pro-inflammatory cytokine using western blotting and/or using ELISA or a suitable assay. More preferably, an increase of the expression level of a polypeptide means an increase of at least 10%, even more preferably at least 20%, at least 30%, at least 40%, at least 50%, at least 70%, at least 90%, at least 150%, or more.

Preferably, an increase of a pro-inflammatory cytokine activity means an increase of at least 5% of the polypeptide activity using a suitable assay. More preferably, an increase of the polypeptide activity means an increase of at least 10%, even more preferably at least 20%, at least 30%, at least 40%, at least 50%, at least 70%, at least 90%, at least 150% or more. In a most preferred diagnostic method, Lyme disease is diagnosed when the detection or comparison leads to the finding of a detectable level or an increase of the level of expression of a pro-inflammatory cytokine or an increase or a detection of the expression level of a nucleotide sequence encoding said pro-inflammatory cytokine, said detection or increase being detected at the level of the amino acid sequence of said pro-inflammatory cytokine, more preferably an increase of at least 5% of the expression level of said pro-inflammatory cytokine using ELISA as defined herein.

The method of the invention is attractive since the diagnosis is reached early enough in order to treat a diagnosed subject to prevent damage. Furthermore, this method is non-invasive, simple, reproducible, sensitive, specific, and time and cost efficient.

Assay Device

In a second aspect, an assay device is provided for diagnosing Lyme disease in a subject, wherein said device comprises a molecule which specifically binds a pro-inflammatory cytokine. This device may be used in a diagnosis method of the invention. Any subject or physician could use this device at office/home, repeat the use of such device as often as necessary. Preferably, a pro-inflammatory cytokine is IL-1β. The type of molecules that are known to specifically bind a pro-inflammatory cytokine have already been earlier described herein. In a preferred embodiment, a molecule which specifically binds a pro-inflammatory cytokine and which is present in the device is an antibody.

In a preferred embodiment, an assay device is a lateral flow test strip also known as dipstick, preferably, though not necessarily, encased in a housing, designed to be read by the subject, and the assay is a sandwich immunoassay. Such devices are impregnated with reagents that specifically indicate the presence of a given molecule, here a cytokine by changing colour upon contact with a sample. Preferred subject's samples have already been defined herein. An antibody is preferably labelled by conjugation to a physically detectable label, and upon contacting with a sample containing a pro-inflammatory cytokine forms a complex. Said antibody-pro-inflammatory cytokine complex is then contacted with a second antibody, which recognizes said first antibody and which is immobilized on a solid support within the device. A second antibody captures said antibody-pro-inflammatory cytokine complex to form an antibody-pro-inflammatory cytokine-antibody sandwich complex, and the resulting complex, which is immobilized on the solid support, is detectable by virtue of the label. A test strip may then be inserted into a reader, where a signal from said label in the complex is measured. Alternatively, a test strip could be inserted into the reader prior to addition of the sample. Alternatively and according to a preferred embodiment, the presence of a pro-inflammatory cytokine is visualised by a subject as a change of colour of at least part of a device. Dipsticks are usually made of paper or cardboard. Usually additional molecules are present in a device as a positive or negative control. A typical positive control could be an antibody recognizing a molecule which is known to be present in a sample to be tested. A typical negative control could be an antibody recognizing a molecule which is known to be absent in a sample to be tested.

Kit of Parts

In a further aspect, there is provided a kit of parts for diagnosing Lyme disease in a subject comprising a) a source of *Borrelia* antigens and b) reagents for detecting the expression level of a pro-inflammatory cytokine.

Each feature of this kit has already been defined herein.

In a preferred kit, the molecule which specifically binds a pro-inflammatory cytokine is an antibody.

Peptidomimetic or Peptide Mimetic

A peptide-like molecule (referred to as peptidomimetic) or non-peptide molecule that specifically binds to a cytokine as defined herein and that may be applied in a method of the invention as defined herein may be identified using a method known in the art per se, as e.g. described in detail in U.S. Pat. No. 6,180,084 which incorporated herein by reference. Such a methods includes e.g. screening libraries of peptidomimetics, peptides, DNA or cDNA expression libraries, combinatorial chemistry and, particularly useful, phage display libraries. These libraries may be screened for an agonists and/or an antagonist of said cytokine by contacting the libraries with a substantially purified polypeptide of the invention, fragments thereof or structural analogues thereof.

Sequence Identity

"Sequence identity" is herein defined as a relationship between two or more amino acid (polypeptide or protein) sequences or two or more nucleic acid (polynucleotide) sequences, as determined by comparing the sequences. The identity between two amino acid or two nucleic acid sequences is preferably defined by assessing their identity within a whole SEQ ID NO as identified herein or part thereof. Part thereof may mean at least 50% of the length of the SEQ ID NO, or at least 60%, or at least 70%, or at least 80%, or at least 90%.

In the art, "identity" also means the degree of sequence relatedness between amino acid or nucleic acid sequences, as the case may be, as determined by the match between strings of such sequences. "Similarity" between two amino acid sequences is determined by comparing the amino acid sequence and its conserved amino acid substitutes of one polypeptide to the sequence of a second polypeptide. "Identity" and "similarity" can be readily calculated by known methods, including but not limited to those described in (Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heine, G., Academic Press, 1987; and Sequence Analysis Primer, Gribskov, M. and Devereux, J., eds., M Stockton Press, New York, 1991; and Carillo, H., and Lipman, D., SIAM J. Applied Math., 48:1073 (1988).

Preferred methods to determine identity are designed to give the largest match between the sequences tested. Methods to determine identity and similarity are codified in publicly available computer programs. Preferred computer program methods to determine identity and similarity between two sequences include e.g. the GCG program package (Devereux, J., et al., Nucleic Acids Research 12 (1): 387 (1984)), BestFit, BLASTP, BLASTN, and FASTA (Altschul, S. F. et al., J. Mol. Biol. 215:403-410 (1990). The BLAST X program is publicly available from NCBI and other sources (BLAST Manual, Altschul, S., et al., NCBI NLM NIH Bethesda, Md. 20894; Altschul, S., et al., J. Mol. Biol. 215:403-410 (1990). The well-known Smith Waterman algorithm may also be used to determine identity.

Preferred parameters for polypeptide sequence comparison include the following: Algorithm: Needleman and Wunsch, J. Mol. Biol. 48:443-453 (1970); Comparison matrix: BLOSSUM62 from Hentikoff and Hentikoff, Proc. Natl. Acad. Sci. USA. 89:10915-10919 (1992); Gap Penalty: 12; and Gap Length Penalty: 4. A program useful with these parameters is publicly available as the "Ogap" program from Genetics Computer Group, located in Madison, Wis. The aforementioned parameters are the default parameters for amino acid comparisons (along with no penalty for end gaps).

Preferred parameters for nucleic acid comparison include the following: Algorithm: Needleman and Wunsch, J. Mol. Biol. 48:443-453 (1970); Comparison matrix: matches=+10, mismatch=0; Gap Penalty: 50; Gap Length Penalty: 3. Available as the Gap program from Genetics Computer Group, located in Madison, Wis. Given above are the default parameters for nucleic acid comparisons.

Optionally, in determining the degree of amino acid similarity, the skilled person may also take into account so-called "conservative" amino acid substitutions, as will be clear to the skilled person. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulphur-containing side chains is cysteine and methionine. Preferred conservative amino acids substitution groups are: valine-leucine-isoleucine, phenylalanine-tyrosine, lysine-arginine, alanine-valine, and asparagine-glutamine. Substitutional variants of the amino acid sequence disclosed herein are those in which at least one residue in the disclosed sequences has been removed and a different residue inserted in its place. Preferably, the amino acid change is conservative. Preferred conservative substitutions for each of the naturally occurring amino acids are as follows: Ala to Ser; Arg to Lys; Asn to Gln or His; Asp to Glu; Cys to Ser or Ala; Gln to Asn; Glu to Asp; Gly to Pro; His to Asn or Gln; Ile to Leu or Val; Leu to Ile or Val; Lys to Arg, Gln or Glu; Met to Leu or Ile; Phe to Met, Leu or Tyr; Ser to Thr; Thr to Ser; Trp to Tyr; Tyr to Trp or Phe; and Val to Ile or Leu.

Antibodies

Some aspects of the invention concern the use of an antibody or antibody-fragment that specifically binds a pro-inflammatory cytokine Methods for generating antibodies or antibody-fragments that specifically bind to a polypeptide are described in e.g. Harlow and Lane (1988, Antibodies: A Laboratory Manual, Cold Spring Harbor Laboratory Press, Cold Spring Harbor, N.Y.) and WO 91/19818; WO 91/18989; WO 92/01047; WO 92/06204; WO 92/18619; and U.S. Pat. No. 6,420,113 and references cited therein. The term "specific binding," as used herein, includes both low and high affinity specific binding. Specific binding can be exhibited, e.g., by a low affinity antibody or antibody-fragment having a Kd of at least about $10^{-4}$ M. Specific binding also can be exhibited by a high affinity antibody or antibody-fragment, for example, an antibody or antibody-fragment having a Kd of at least about of $10^{-7}$ M, at least about $10^{-8}$ M, at least about $10^{-9}$ M, at least about $10^{-10}$ M, or can have a Kd of at least about $10^{-11}$ M or $10^{-12}$ M or greater.

General

In this document and in its claims, the verb "to comprise" and its conjugations is used in its non-limiting sense to mean that items following the word are included, but items not specifically mentioned are not excluded. In addition the verb "to consist" may be replaced by "to consist essentially of" meaning that a method or an assay device as defined herein may comprise additional step(s), respectively component(s) than the ones specifically identified, said additional step(s), respectively component(s) not altering the unique characteristic of the invention. In addition, reference to an element by the indefinite article "a" or "an" does not exclude the possibility that more than one of the element is present, unless the context clearly requires that there be one and only one of the elements. The indefinite article "a" or "an" thus usually means "at least one". The word "about" when used in association with an integer (about 10) preferably means that the value may be the given value of 10 more or less 1 of the value: about 10 preferably means from 9 to 11. The word "about" when used in association with a numerical value (about 10.6) preferably means that the value may be the given value of 10.6 more or less 1% of the value 10.6.

All patent and literature references cited in the present specification are hereby incorporated by reference in their entirety. The following examples are offered for illustrative purposes only, and are not intended to limit the scope of the present invention in any way.

EXAMPLES

Example 1

FIGS. 1, 2

Figure 2:
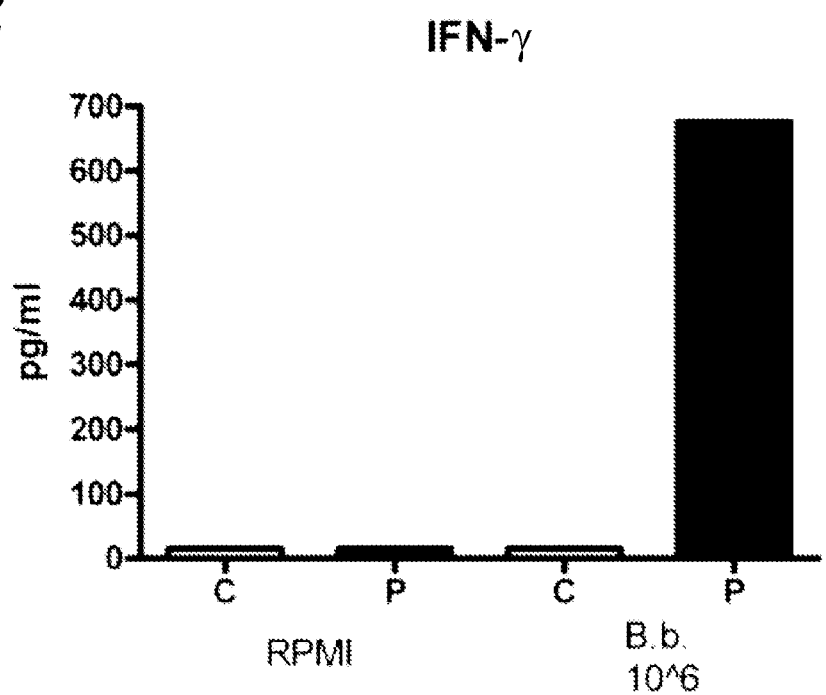
FIG. 2 Peripheral blood mononuclear cells (PBMC) were isolated from healthy volunteers (C) and patients with Lyme disease (P). $1.10^6$ cells/ml were stimulated for 48 h with *Borrelia* species ($1.10^5$/ml). Thereafter IFNγ was determined by ELISA.
Figure 3A:
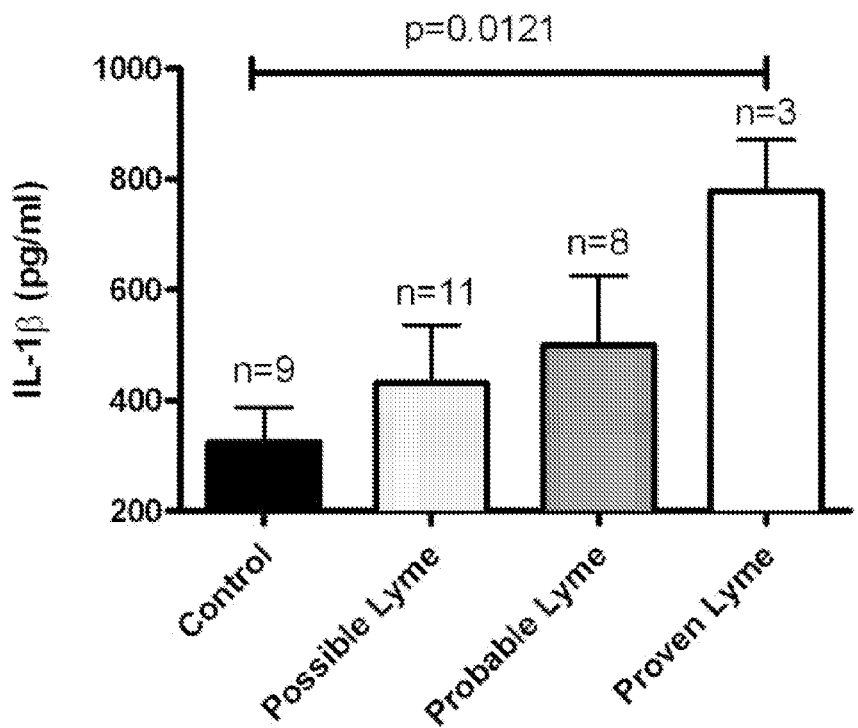
FIG. 3 Peripheral blood mononuclear cells (PBMC) were isolated from control, possible, probable and proven Lyme patients and stimulated with $1.10^6$ *Borrelia burgdoferi* cells/ml for 24 h. Thereafter IFNγ or IL-1β was determined by ELISA.
Figure 3B:
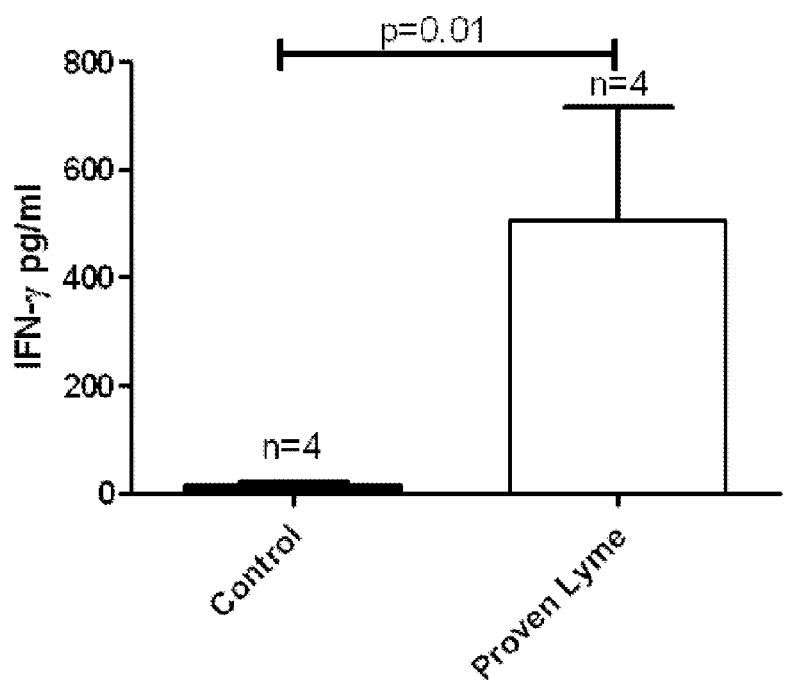

Peripheral blood mononuclear cells (PBMC) were isolated from healthy volunteers (C) and patients with Lyme disease (P). $1.10^6$ cells/ml were stimulated in RPMI 1640 for 24 h with the following strains of Borrelia: B. burgdorferi (ATCC 35210), B. garinii (ATCC 51383) and B. afzelii (ATCC 51567) that were first heat-inactivated by heating at 52° C. for 30 minutes ($1.10^5$/ml). Thereafter IL-1β was determined by ELISA using antibody from R&D systems (IL-1F2). IL-1β was strongly detected in Lyme patients (see FIGS. 1, 2).

Blood (lithiumheparine) was taken from a subject suspected to have the Lyme disease. Blood was subsequently diluted in culture medium (1:5) and stimulated for 4 hours with 3 species of Borrelia common in Europe (see above). Subsequently, the supernatant was isolated via centrifugation and the presence of IL-1b was assessed by ELISA as described above.

Example 3

FIG. 3

Venous blood was drawn from the cubital vein of healthy volunteers and Lyme patients into 10 mL ethylenediaminetetraacetic acid (EDTA) tubes (Monoject). Peripheral blood mononuclear cells (PBMCs) were isolated according to standard protocols, with minor modifications. The PBMC fraction was obtained by density centrifugation of blood diluted 1:1 in PBS over Ficoll-Pague (Pharmacia Biotech). Cells were washed three times in PBS and resuspended in RPMI 1640 (Dutch modified) supplemented with 50 mg/L gentamycin, 2 mM L-glutamin, and 1 mM pyruvate. Cells were counted in a Coulter Counter Z® (Beckman Coulter), and adjusted to $5 \times 10^6$ cells/mL. Mononuclear cells ($5 \times 10^5$) in a 100 µL volume were added to round-bottom 96-wells plates (Greiner) and incubated with either 100 µL of medium (negative control) or B. burgdorferi (ATCC 35210), at a dose of $1 \times 10^6$ spirochetes per mL. The B. burgdorferi were first heat-inactivated by heating at 52° C. for 30 minutes. Concentrations of human IL-1β or IFN-γ were determined using either specific or commercial ELISA kits (R&D Systems, Minneapolis or Pelikine Sanquin, Amsterdam, The Netherlands), in accordance with the manufacturers' instructions. Detection limits were 40 pg/mL for IL-1β and for IFN-γ ELISA (12 pg/mL).

Example 4

Blood samples were taken from patients and healthy individuals in EDTA vacutainer tubes (Becton and Dickinson, Leiden, The Netherlands). From these samples 200 µl were diluted 1:5 in culture medium (RPMI 1640) and incubated in 24 wells tissue culture plates (Costar, Badhoevedorp, The Netherlands). As a stimulus, 100 ng/ml of formaldehyde-inactivated (i.e. formalin fixated) B. burgdorferi (ATCC 35210), B. garinii (ATCC 51383) or B. afzelii (ATCC 51567) that were first heat-inactivated by heating at 52° C. for 30 minutes was added to these cultures. Formaldehyde-inactivated cells were prepared by transferring or incubating them with 4% formaldehyde for one hour. Subsequently cells were washed several times with PBS. No stimulus was added to the control cultures. The cultures were incubated at 37° C. and 5% CO2 for 48 hours. After this incubation period, the supernatants were harvested and centrifuged at 15000 g for 5 minutes, and thereafter stored at −20° C. until measurement of interferon γ (IFNγ) and/or IL-β.

IFN γ was measured using a specific ELISA (Pelikine Sanquin, Amsterdam, The Netherlands). IL-1β was measured as described in example 1.

The invention claimed is:

1. A method for diagnosing Lyme disease in a subject, the method comprising the steps of:
   (a) contacting a sample obtained from said subject with a source of *Borellia* antigen from a species of *Borellia* selected from the group consisting of *B. burgdorferi, B. garinii, B. afzelii* and combinations thereof, wherein said sample comprises peripheral blood mononuclear cells (PBMC);
   (b) determining a protein expression level of IL-1β in said sample at the end of step (a); and
   (c) diagnosing Lyme disease in said subject when a detectable expression level or an increase of the expression level of IL-1β is determined in step (b).

2. A method according to claim 1, wherein the protein expression level of IL-1β is determined by directly quantifying an amount of said IL-1β in said sample using a molecule which specifically binds to IL-1β.

3. A method according to claim 1, wherein said source of *Borrelia* antigen is a whole *Borrelia* cell.

4. A method according to claim 1, wherein the sample is a fluid obtained from the subject.

5. A method according to claim 4, wherein the fluid is blood.

6. A method according to claim 1, wherein in (a) if several species of *Borrelia* are used as a source of *Borrelia* antigens, the sample of step (a) is divided into several sub-samples, each sub-sample being contacted with a source of antigens from one species of *Borrelia*.

7. A method according to claim 2, wherein the molecule which specifically binds IL-1β is an antibody.

8. A device method according to claim 2, wherein step (b) is performed using a lateral flow test strip which comprises the molecule which specifically binds to IL-1β.

9. A method according to claim 3, wherein the *Borrelia* cell is heat-inactivated or formalin-fixated.

10. A method according to claim 1, wherein the protein expression level of IL-1β is determined by directly quantifying an amount of said IL-1β in said sample using an immunoassay.

11. A method according to claim 10, wherein said immunoassay is selected from the group consisting of western blotting, ELISA and FACS using latex beads.

12. A method according to claim 10, wherein said immunoassay is a sandwich immunoassay.

13. A method according to claim 1, wherein in (c) Lyme disease is diagnosed in said subject when a detectable expression level of the protein expression level of IL-1β is determined in step (b).

14. A method according to claim 13, wherein the detectable expression level of the protein expression level of IL-1β in (b) is compared to a reference value.

15. A method according to claim 14, wherein said reference value is determined in a control sample.

16. A method according to claim 13, wherein the detectable expression level of the protein expression level of IL-1β in (b) is greater than 40 pg/mL.

17. A method according to claim 1, wherein in (c) Lyme disease is diagnosed in said subject when an increase of the protein expression level of IL-1β is determined in step (b).

18. A method according to claim 17, wherein the increase of the protein expression level of IL-1β is determined by comparison with a protein expression level of IL-1β in a control sample.

19. A method according to claim 1, wherein the sample is diluted blood.

20. A method according to claim 1, wherein the sample comprises peripheral blood mononuclear cells (PBMC) that have been isolated by centrifugation of diluted blood obtained from the subject.

21. A method according to claim 1, wherein in (a) the contacting has a duration of at least 4 hours.

22. A method according to claim 21, wherein in (a) the contacting has a duration of 4-96 hours.

23. A method according to claim 3, wherein in (a) at least $10^4$ whole *Borrelia* cells are contacted with said sample.

24. A method according to claim 1, wherein the species of *Borellia* is selected from the group consisting of strain ATCC 35210 of *B. burgdorferi*, strain ATCC 51383 of *B. garinii*, strain ATCC 51567 of *B. afzelii*, and combinations thereof.

25. A method according to claim 3, wherein the *Borrelia* cell is heat-killed.

26. A method according to claim 1, wherein said source of *Borrelia* antigen is part of a *Borrelia* cell.

27. A method according to claim 26, wherein said part of a *Borrelia* cell is a protein, a digest of the protein and/or a fragment thereof.

28. A method according to claim 26, wherein said part of *Borrelia* cell is a lysate, sonicate or fixate of a *Borrelia* cell.

29. A method according to claim 1, wherein the detectable expression level or the increase of the expression level of IL-1β is determined by comparison to a reference value.

30. A method according to claim 1, wherein the detectable expression level or the increase of the expression level of IL-1β is determined by comparison to a control sample.

31. A method for diagnosing Lyme disease in a subject, the method comprising the steps of:
   (a) contacting a sample obtained from said subject with a source of *Borellia* antigen from a species of *Borellia* selected from the group consisting of *B. burgdorferi, B. garinii, B. afzelii* and combinations thereof, wherein said sample comprises peripheral blood mononuclear cells (PBMC);
   (b) determining protein expression of IL-1β in said sample at the end of step (a); and
   (c) diagnosing Lyme disease in said subject when detectable expression of IL-1β is determined in step (b).

* * * * *

UNITED STATES PATENT AND TRADEMARK OFFICE
CERTIFICATE OF CORRECTION

PATENT NO.        : 9,316,652 B2
APPLICATION NO.   : 13/824321
DATED             : April 19, 2016
INVENTOR(S)       : Leonardus Antonius Bernardus Joosten et al.

It is certified that error appears in the above-identified patent and that said Letters Patent is hereby corrected as shown below:

IN THE CLAIMS

Column 35, line number 43 (claim 8, line 1), delete "device".

Signed and Sealed this
Fifth Day of July, 2016

Michelle K. Lee
*Director of the United States Patent and Trademark Office*

SEQUENCE LISTING

```
<160> NUMBER OF SEQ ID NOS: 10

<210> SEQ ID NO 1
<211> LENGTH: 14020
<212> TYPE: DNA
<213> ORGANISM: Homo sapiens

<400> SEQUENCE: 1
gtagaataca gcaacgacag acattttggg agagaagcat tttatcatag cttttagaag      60
agaagtattt ttcagcatca taagcacaca attccaagga cagatacctt caagggattg     120
cttttgacag ttatgacaaa gtcttaaaga agaataaaag gacaaaggaa atcctccagc     180
aacaaagctg ccacttatag atgagaaagt gaatgggaat aaggaagaaa ctcagaaaag     240
ggaagagaga tcactaaaaa ccctgatttg gaaagtccca gtactaccct gagaggagaa     300
agaaacaaat tcacacagca cgtcaccgcc agaagaagaa aggagggaag acaagggaac     360
agagaggatc tcaatcctaa aaggacaatg tggaaacatt taggggacag aggtgaatct     420
gccaggccaa tgtagtttag aatgtcactc aatcactgag aatgagaaag gagtctgccg     480
atgggcacca tgtggacagg agatgaggca ataaacatat gtaacaatta aaagtgagaa     540
ataaagatct ggttttggtt cagttaaccc atatttgagt cgtagttcca gcatttactg     600
tttgtgcggt cttaaataat ttattgtctc aacctcagtt tctgcatagg tcaaatggtt     660
caatattatc tactttaaag gttattatga agagttaata agataatgag ggaaaaaaag     720
gtacctggca cttagtaggt gctcaataaa ggacggcttt tttttttttaa gtattgcttc     780 taaatttgta tgtaagaaaa aatgatataa tacaatgata taagacaggg gaccgcagga     840
caagtccagc cacacccatt catttatgta ttatctgact gctttctga aatgatgcaa      900 ggttgagtag ttgtacctga aacatttatt atctggccct ttacagaaaa tgtttccaga     960
ccctggataa gtggtaccag agcccctct gtttgtggtc ccctctctta tacccactag    1020
gtgtgagaaa agacatagag taggagagcc ctgccatcca tcttacccac ccaggggctt    1080
tttctgatgg atccaaagga aggacaaggt cttattggtc tcccagaact gacataacaa    1140
ctccgacatc agggaaaagc cattggagac tacatagctc gccagcccca gccacctgct    1200
catatatcta agccctcctt gttctagacc agggaggaga atggaatgtc ccttggactc    1260
tgcatgtccc caatctgaga acctggatcc aagagggaga agaagcccat tggagatgat    1320
gccataaagg aagtggaagc gatatgataa aaatcatagt gcccattccc aaataatccc    1380
agaagcagaa gggaaaggag agaaatatcc acaaagacag gtgtgggtac acacaacatt    1440
tttcatactt taagatccca gagggactca tggaaatgat acaagaaaat gactcataag    1500
aacaaatatt aggaagccag tgccaagaat gagatggaa attggggaaa atgttggggg    1560
cagattgctt agttctgttc taagcaagag ggtgaacaag gaaggaacag ctcactacaa    1620
agaacagaca tcactgcatg tacacacaat aatataagaa ctaacccatg attattttgc    1680
ttgtcttctt gttcaaaatg attgaagacc aatgagatga gatcaacctt gataactggc    1740
tgcgaagccc atgattagac acaagatggt atcagggcac ttgctgcttt gaataaatgt    1800
cagtctcctg tcttggaaga atgacctgac agggtaaaga ggaacttgca gctgagaaag    1860
```

```
gctttagtga ctcaagagct gaataattcc ccaaaagctg gagcatcctg gcatttccag    1920
ctccccatct ctgcttgttc cacttccttg gggctacatc accatctaca tcatcatcac    1980
tcttccactc cctcccttag tgccaactat gtttatagcg agatattttc tgctcattgg    2040
ggatcggaag gaagtgctgt ggcctgagcg gtctccttgg gaagacagga tctgatacat    2100
acgttgcaca acctatttga cataagaggt ttcacttcct gagatggatg ggatggtagc    2160
agatttgggt ccaggttaca gggccaggat gagacatggc agaactgtgg agactgttac    2220 gtcaggggc attgccccat ggctccaaaa tttccctcga gcgaaagcat caggggctca    2280
tgcaacctgg atactagtgc tgcttcaacc acactgtgct attggatgag tcacttccac    2340
cctcctagcc ttgatttctt cgtctgctgt tcacattcaa atagctattc atgtcttcat    2400
ctctgtggtc ccaccatatc ccaccagaca atcattaggg ctcctcttag ctggcagatt    2460
ctgaggtcct ggatgctaca attggaagat ggagaagtag aagctcaagg tttctgacct    2520
gtatcccaag tccagaagc agaatggact aactcagagc tgatgctcgg gtcccttgca    2580
tatctccctt cctgtcactg gctttgatcc tccttcgttc agcttgtaat cacatcaaca    2640
gaccaaagac atctctgtgt tctgtcagga gagttcacag agccaccaac cctccagacc    2700
ctgctggttg ccgcataaag actctgagga agggtttgag gctgctgtga tcatgcaatg    2760
aatgcatgat tgtaccactg cactccagcc tggggataa aggtagatcc tgtctaggag    2820
agagagagag agaaagagaa agagagagag aagggaggga gagacaaaga aaagagaga    2880 gagggaggga gaaagaaaga gagaaagaaa agagaaaaga agaaaaaga aagaaagaga    2940 gagagggagg gagggagaga gaaagaaaga agaaagaga agagagaaa gagagaaaga    3000 gaaagaaagg aagaaagaaa gaagaaaaga agaaagaaa gaaagaaaga agaaaagaa    3060 aagaaagaaa gagagagaga agaaaaaga aagaggaagg aaggaaggaa ggaagaaaga    3120
caggctctga ggaaggtggc agttcctaca acgggagaac cagtggttaa tttgcaaagt    3180
ggatcctgtg gaggcaaaac agaggagtcc cctaggccac ccagacaggg cttttagcta    3240
tctgcaggac cagacaccaa atttcaggag ggctcagtgt taggaatgga ttatggctta    3300
tcaaattcac aggaaactaa catgttgaac agcttttaga tttcctgtgg aaaatataac    3360
ttactaaaga tggagttctt gtgactgact cctgatatca agatactggg agccaaatta    3420
aaaatcagaa ggctgcttgg agagcaagtc catgaaatgc tcttttttccc acagtagaac    3480 ctatttccct cgtgtctcaa atacttgcac agaggctcac tcccttggat aatgcagagc    3540
gagcacgata cctggcacat actaatttga ataaaaatgc tgtcaaattc ccattcaccc    3600
attcaagcag caaactctac cacctgaatg tacatgccag gcactgtgct agacttggct    3660
caaaaagatt tcagtttcct ggaggaacca ggaggagcaa ggtttcaact cagtgctata    3720
agaagtgtta caggctggac acggtggctc acgcctgtaa tcccaacact ttgggaggcc    3780
gaggcgggca gatcacaagg tcaggagatc gagaccatcc tggctaacat ggtgaaaccc    3840
tgtctctact aaaaatacaa aaaattagcc gggcgtggcg gcaggtgcct gtagtcccag    3900
ctgctgggga ggctgaggca ggagaatggt gtgaacccgg gaggcggaac ttgcaggggg    3960
ccgagatcgt gccactgcac tccagcctgg gcgacagagt gagactctgt ctcaaaaaaa    4020 aaaaaaagt gttatgatgc agacctgtca agaggcaaa ggagggtgtt cctacactcc    4080
aggcactgtt cataacctgg actctcattc attctacaaa tggagggctc ccctgggcag    4140
taccctggag caggcacttt gctggtgtct cggttaaaga gaaactgata actcttggtt    4200
```

-continued

```
ggtattacca agagatagag tctcagatgg atattcttac agaaacaata ttccactttt      4260
cagagttcac caaaaaatca ttttaggcag agctcatctg cattgatct ggttcatcca       4320 tgagattggc tagggtaaca gcacctggtc ttgcagggtt gtgtgagctt atctccaggg      4380
ttgccccaac tccgtcagga gcctgaaccc tgcataccgt atgttctctg ccccagccaa      4440
gaaaggtcaa ttttctcctc agaggctcct gcaattgaca gagagctcct gaggcagaga      4500
acagcaccca aggtagagac ccacaccctc aatacagaca ggggagggcta ttggcccttc     4560 attgtaccca tttatccatc tgtaagtggg aagattccta aacttaagta caaagaagtg     4620
aatgaagaaa agtatgtgca tgtataaatc tgtgtgtctt ccactttgtc ccacatatac      4680
taaatttaaa cattcttcta acgtgggaaa atccagtatt ttaatgtgga catcaactgc      4740
acaacgattg tcaggaaaac aatgcatatt tgcatggtga tacatttgca aaatgtgtca      4800
tagtttgcta ctccttgccc ttccatgaac cagagaatta tctcagttta ttagtcccct     4860
cccctaagaa gcttccacca atactctttt cccctttcct ttaacttgat tgtgaaatca      4920
ggtattcaac agagaaattt ctcagcctcc tacttctgct tttgaaagcc ataaaaacag      4980
cgagggagaa actggcagat accaaacctc ttcgaggcac aaggcacaac aggctgctct      5040
gggattctct tcagccaatc ttcattgctc aagtatgact ttaatcttcc ttacaactag      5100
gtgctaaggg agtctctctg tctctctgcc tctttgtgtg tatgcatatt ctctctctct      5160
ctctctttct ttctctgtct ctccctctcc ttccctctct gcctccctct ctcagctttt     5220
tgcaaaaatg ccaggtgtaa tataatgctt atgactcggg aaatattctg ggaatggata     5280
ctgcttatct aacagctgac accctaaagg ttagtgtcaa agcctctgct ccagctctcc      5340
tagccaatac attgctagtt ggggtttggt ttagcaaatg cttttctcta gacccaaagg      5400
acttctcttt cacacattca ttcatttact cagagatcat ttctttgcat gactgccatg     5460
cactggatgc tgagagaaat cacacatgaa cgtagccgtc atggggaagt cactcatttt     5520
ctccttttta cacaggtgtc tgaagcagcc atggcagaag tacctgagct cgccagtgaa     5580
atgatggctt attacaggtc agtggagacg ctgagaccag taacatgagc aggtctcctc     5640
tttcaagagt agagtgttat ctgtgcttgg agaccagatt ttttcccctaa attgcctctt      5700 tcagtggcaa acagggtgcc aagtaaatct gatttaaaga ctactttccc attacaagtc     5760
cctccagcct tgggacctgg aggctatcca gatgtgttgt tgcaagggct tcctgcagag     5820
gcaaatgggg agaaaagact ccaagcccac aatacaagga atcccttgc aaagtgtggc      5880 ttggagggag agggagagct cagattttag ctgactctgc tgggctagag gttaggcctc     5940
aagatccaac agggagcacc cagggtgccc acctgccagg cctagaatct gccttctgga     6000
ctgttctgcg catatcactg tgaaacttgc caggtgtttc aggcagcttt gagaggcagg      6060
ctgtttgcag tttcttatga acagtcaagt cttgtacaca gggaaggaaa aataaacctg      6120
tttagaagac ataattgaga catgtccctg ttttttattac agtggcaatg aggatgactt      6180
gttctttgaa gctgatggcc ctaaacagat gaaggtaaga ctatgggttt aactcccaac      6240
ccaaggaagg gctctaacac agggaaagct caaagaaggg agttctgggc cactttgatg      6300
ccatggtatt tgtttttaga aagactttaa cctcttccag tgagacacag gctgcaccac      6360
ttgctgacct ggccacttgg tcatcatatc accacagtca ctcactaacg ttggtggtgg      6420
tggccacact tggtggtgac aggggaggag tagtgataat gtttcccatt tcatagtagg      6480
aagacaacca agtcttcaac ataaatttga ttatccttt aagagatgga ttcagcctat       6540
gccaatcact tgagttaaac tctgaaacca agagatgatc ttgagaacta acatatgtct      6600
```

```
accccttttg agtagaatag ttttttgcta cctggggtga agcttataac aacaagacat    6660
agatgatata aacaaaaaga tgaattgaga cttgaaagaa aaccattcac ttgctgtttg    6720
accttgacaa gtcattttac ccgctttgga cctcatctga aaataaagg gctgagctgg     6780 atgatctctg agattccagc atcctgcaac ctccagttct gaaatatttt cagttgtagc    6840
taagggcatt tgggcagcaa atggtcattt ttcagactca tccttacaaa gagccatgtt    6900
atattcctgc tgtcccttct gttttatatg atgctcagta gccttcctag gtggcccagc    6960
catcagccta gctaggtcag ttgtgcaggt tgggaggcag ccacttttct ctggctttat    7020
tttattccag tttgtgatag cctcccctag cctcataatc cagtcctcaa tcttgttaaa    7080
aacatatttc tttagaagtt ttaagactgg cataacttgt tggctgcagc tgtgggagga    7140
gcccattggc ttgtctgcct ggcctttgcc cccattgcct cttccagcag cttggctctg    7200
ctccaggcag gaaattctct cctgctcaac tttcttttgt gcacttacag gtctctttaa    7260
ctgtctttca agcctttgaa ccattatcat gccttaaggc aacctcagtg aagccttaat    7320
acggagcttc tctgaataag aggaaagtgg taacatttca caaaagtac tctcacagga     7380 tttgcagaat gcctatgaga cagtgttatg aaaaggaaa aaaagaaca gtgtagaaaa      7440 attgaatact tgctgagtga gcataggtga atggaaaatg ttatggtcat ctgcatgaaa    7500
aagcaaatca tagtgtgaca gcattaggga tacaaaaaga tatagagaag gtatacatgt    7560
atggtgtagg tggggcatgt acaaaaaaga tgaacaaagt agaaatggga tttattctaa    7620
aagaatagcc tgtaaggtgt cagaaagccc acattctagt cttgagtctg cctctaacct    7680
gctgtgtgcc cttgagtaca cacttaacct ccttgagctt cagagaggga taatcttttt    7740
attttatttt attttatttt gttttgtttt gttttgtttt gttttatgag acagagtctc    7800
actctgttgc ccaggctgga gtgcagtggt acaatcttgg cttactgcat cctccacctc    7860
ctgagttcaa gcgattctcc ttcctcagtc tcctgaatag ctaggattac aggtgcaccc    7920
caccacaccc agctaatttt tgtattttta gtagagaagg ggtttcgcca tgttggccag    7980
gctggttttg aagtcctgac ctaaatgatt catccacctc ggcttcccaa agtgctggga    8040
ttacaggcat gagccaccac gcctggccca gagagggatg atctttagaa gctcgggatt    8100
ctttcaagcc cttcctcct  ctctgagctt tctactctct gatgtcaaag catggttcct    8160
ggcaggacca cctcaccagg ctccctccct cgctctctcc gcagtgctcc ttccaggacc    8220
tggacctctg ccctctggat ggcggcatcc agctacgaat ctccgaccac cactacagca    8280
agggcttcag gcaggccgcg tcagttgttg tggccatgga caagctgagg aagatgctgg    8340
ttccctgccc acagaccttc caggagaatg acctgagcac cttcttcccc ttcatctttg    8400
aagaaggtag ttagccaaga gcaggcagta gatctccact tgtgtcctct tggaagtcat    8460
caagccccag ccaactcaat tcccccagag ccaaagccct ttaaaggtag aaggcccagc    8520
ggggagacaa aacaaagaag gctggaaacc aaagcaatca tctctttagt ggaaactatt    8580
cttaaagaag atcttgatgg ctactgacat ttgcaactcc ctcactcttt ctcagggcc     8640 tttcacttac attgtcacca gaggttcgta acctccctgt gggctagtgt tatgaccatc    8700 accatttac ctaagtagct ctgttgctcg gccacagtga gcagtaatag acctgaagct     8760
ggaacccatg tctaatagtg tcaggtccag tgttcttagc cacccactc ccagcttcat     8820 ccctactggt gttgtcatca gactttgacc gtatatgctc aggtgtcctc caagaaatca    8880
aattttgccg cctcgcctca cgaggcctgc ccttctgatt ttatacctaa acaacatgtg    8940
```

```
ctccacattt cagaacctat cttcttcgac acatgggata acgaggctta tgtgcacgat    9000
gcacctgtac gatcactgaa ctgcacgctc cgggactcac agcaaaaaag cttggtgatg    9060
tctggtccat atgaactgaa agctctccac ctccagggac aggatatgga gcaacaaggt    9120
aaatggaaac atcctggttt ccctgcctgg cctcctggca gcttgctaat tctccatgtt    9180
ttaaacaaag tagaaagtta atttaaggca aatgatcaac acaagtgaaa aaaatatta    9240 aaaaggaata tacaaacttt ggtcctagaa atggcacatt tgattgcact ggccagtgca    9300
tttgttaaca ggagtgtgac cctgagaaat tagacggctc aagcactccc aggaccatgt    9360
ccacccaagt ctcttgggca tagtgcaatg tcaattcttc cacaatatgg ggtcatttga    9420
tggacatggc ctaactgcct gtgggttctc tcttcctgtt gttgaggctg aaacaagagt    9480
gctggagcga taatgtgtcc atcccctcc ccagtcttcc cccttgccc caacatccgt     9540 cccacccaat gccaggtggt tccttgtagg gaaattttac cgcccagcag gaacttatat    9600
ctctccgctg taacgggcaa aagtttcaag tgcggtgaac ccatcattag ctgtggtgat    9660
ctgcctggca tcgtgccaca gtagccaaag cctctgcaca ggagtgtggg caactaaggc    9720
tgctgacttt gaaggacagc ctcactcagg gggaagctat ttgctctcag ccaggccaag    9780
aaaatcctgt ttctttggaa tcgggtagta agagtgatcc cagggcctcc aattgacact    9840
gctgtgactg aggaagatca aaatgagtgt ctctcttgg agccactttc ccagctcagc    9900
ctctcctctc ccagtttctt cccatgggct actctctgtt cctgaaacag ttctggtgcc    9960
tgatttctgg cagaagtaca gcttcacctc tttcctttcc ttccacattg atcaagttgt   10020
tccgctcctg tggatgggca cattgccagc cagtgacaca atggcttcct tccttccttc   10080
cttcagcatt taaaatgtag accctctttc attctccgtt cctactgcta tgaggctctg   10140
agaaaccctc aggcctttga ggggaaaccc taaatcaaca aaatgaccct gctattgtct   10200
gtgagaagtc aagttatcct gtgtcttagg ccaaggaacc tcactgtggg ttcccacaga   10260
ggctaccaaa ttacatgtat cctactcatg gggcctaggg gttggggtga ccctgcactg   10320
ctgtgtccct aaccacaaga ccccttctt tcttcagtgg tgttctccat gtcctttgta   10380
caaggagaag aaagtaatga caaaatacct gtggccttgg gcctcaagga aaagaatctg   10440
tacctgtcct gcgtgttgaa agatgataag cccactctac agctggaggt aagtgaatgc   10500
tatgaaatga agcccttctc agcctcctgc taccacttat tcccagacaa ccaccttctc   10560
cccgccccca tccctaggaa aagctgggaa caggtctatt tgacaatttt gcattaatgt   10620
aaataaattt aacataattt ttaactgcgt gcaaccttca atcctgctgc agaaaattaa   10680
atcattttgc cgatgttatt atgtcctacc atagttacaa ccccaacaga ttatatattg   10740
ttagggctgc tctcatttga tagacacctt gggaaataga tgacttaaag ggtcccatta   10800
tcatgtccac tccactccca aaattaccac cactatcacc tccagctttc tcagcaaaag   10860
cttcatttcc aagttgatgt cattctagga ccataaggaa aaatacaata aaagcccct    10920 ggaaactagg tacttcaaga agctctagct taattttcac cccccaaaa aaaaaaaatt    10980 ctcacctaca ttatgctcct cagcatttgg cactaagttt tagaaaagaa gaagggctct   11040
tttaataatc acacggaaag ttgggggccc agttacaact caggagtctg gctcctgatc   11100
atgtgacctg ctcgtcagtt tccttctgg ccaacccaaa gaacatcttt cccatagcat    11160
ctttgtccct tgccccacaa aaattcttct ttctctttcg ctgcagagtg tagatcccaa   11220
aaattaccca agaagaagaa tggaaaagcg atttgtcttc aacaagatag aaatcaataa   11280
caagctggaa tttgagtctg cccagttccc caactggtac atcagcacct ctcaagcaga   11340
```

```
aaacatgccc gtcttcctgg gagggaccaa aggcggccag gatataactg acttcaccat    11400
gcaatttgtg tcttcctaaa gagagctgta cccagagagt cctgtgctga atgtggactc    11460
aatccctagg gctggcagaa agggaacaga aaggttttg agtacggcta tagcctggac    11520
tttcctgttg tctacaccaa tgcccaactg cctgccttag ggtagtgcta agaggatctc    11580
ctgtccatca gccaggacag tcagctctct cctttcaggg ccaatcccca gcccttttgt    11640
tgagccaggc ctctctcacc tctcctactc acttaaagcc cgcctgacag aaaccacggc    11700
cacatttggt tctaagaaac cctctgtcat tcgctcccac attctgatga gcaaccgctt    11760
ccctatttat ttatttattt gtttgtttgt tttattcatt ggtctaattt attcaaaggg    11820
ggcaagaagt agcagtgtct gtaaaagagc ctagttttta atagctatgg aatcaattca    11880
atttggactg gtgtgctctc tttaaatcaa gtcctttaat taagactgaa aatatataag    11940
ctcagattat ttaaatggga atatttataa atgagcaaat atcatactgt tcaatggttc    12000
tgaaataaac ttcactgaag aaaaaaaaag ggtctttcct gatcattgac ttgtcttgga    12060
tttgacactg aacagtaaag acaaacaggg ctgtgagagt tcttggggga ctaaagccca    12120
ctcctcattg ctgagtgctg caaagtacct agaaatatcc ttggccaccg aagactatcc    12180
tcctcaccca tcccctttat ttctgttgtt caacagaagg atattcagtg cacatttgga    12240
acaggatcag ctgaagcact gcagggagtc aggactggta gtaacagcta ccagtgattt    12300
atctatcaat gcaccaaaca tctgttgagc aagcgctatg tactaggagc tgggagtaca    12360
gagatgagaa cagtcacaag tccctcctca gataggagag gcagctagtt ataagcagaa    12420
acaaggtaac atgacaagta gagtaagata agaacaaga ggagtagcca ggaaggaggg    12480
aggagaacga cataagaatc aagcctaaag ggataaacag aagatttcca cacatgggct    12540
gggcatggtg gcttacgcct gtaatcccag cactttgggt ggcaggggca gaaagatcgc    12600
ttgagcccag gagttcaaga ccagcctggg caacatagtg agactcccat ctctacaaaa    12660
aataaataaa taaataaaac aatcagccag gcatgctggc atgcacctgt agtcctagct    12720
acttgggaag ctgacactgg aggattgctt gagcccagaa gttcaagact gcagtgagct    12780
gtgatcgcac cattgcactc cagcctgggt gacagagtga gaccctgtct ctaaaaaatg    12840
ttcccagata gaaaagaaaa gaaaaagccc tcaggtagag gaaccagtgt gaacaagagc    12900
atgggtgtat aagaatgaat gatgcaaaaa gtacactttc agaattgcgg gaatcaccag    12960
aagcaaagtc aaagcgcaaa acaagccaga ggaaaagtag ttgtaactca caccccagat    13020
aaagagataa cttgtttcac atgtaaagaa ctgcctcaaa acatttgaaa aaaaagaaca    13080
aaaatccagc aaaacaagag gcaagggatc ttaacagtct gttcacagaa aagaaaatac    13140
tatttgatct tgggcagagt aaaatgatgc ttaacattgt aataagaaag tcaaattaaa    13200
agcactttga gatactagta ttttcccatc agattgacaa aaatcaaaag tttaacaaca    13260
gaccttgttg gtcaaactgt cgggaaatcc ccactgttaa atattacgcg tgggactata    13320
aattgatatg acccttatag aacaaaattt gctaactatg aaaatcacaa gtgcacttcc    13380
cctttgatcc agcaatttca ctcctggaga tttatcccac agatggacat aacccatgtg    13440
aaatggaaaa tgatcaaaat tattcattgc acatcatttg taataggaaa aattggaagt    13500
aacccaagtg tctatcaaca agagactgcc taaatgaagt aaaggacata gaatactagg    13560
cagctataga aaagaatgag aaagcactct ggtattgttt ggttctgtgt cccagcccaa    13620
atctcatgtc aaattgtaat ccccgatgtt ggaggtgggg cctggtgtgg ggtgattgga    13680
```

-continued

| | | |
|---|---|---|
| tcatgggggt ggagttctta tgaatggttt agcactatcc ctttggtgct gttctcgtga | 13740 | |
| cagagttccc acaagatctg gttgtttaaa agtatgtggc atcctttctc tctctctctc | 13800 | |
| tctctctcag tcctgctcct gccatataag acatccactc ccgctttgtc ttctgcatga | 13860 | |
| gtaaaagctt cctaaggcct ccccagaagc agatgctgcc atgcttcctg tggaacagcc | 13920 | |
| tgcgaagctg tgagccaatt aaacctcttt tctttataaa ttatgcagtc tcaggtattt | 13980 | |
| ccttatagca atgcaaggac tgactaatac atgctgtctg | 14020 | |

<210> SEQ ID NO 2
<211> LENGTH: 1240
<212> TYPE: DNA
<213> ORGANISM: Homo sapiens

<400> SEQUENCE: 2

| | | |
|---|---|---|
| cacattgttc tgatcatctg aagatcagct attagaagag aaagatcagt taagtccttt | 60 | |
| ggacctgatc agcttgatac aagaactact gatttcaact tctttggctt aattctctcg | 120 | |
| gaaacgatga aatatacaag ttatatcttg gcttttcagc tctgcatcgt tttgggttct | 180 | |
| cttggctgtt actgccagga cccatatgta aagaagcag aaaaccttaa gaaatatttt | 240 | |
| aatgcaggtc attcagatgt agcggataat ggaactcttt tcttaggcat tttgaagaat | 300 | |
| tggaaagagg agagtgacag aaaaataatg cagagccaaa ttgtctcctt ttacttcaaa | 360 | |
| cttttttaaaa actttaaaga tgaccagagc atccaaaaga gtgtggagac catcaaggaa | 420 | |
| gacatgaatg tcaagttttt caatagcaac aaaaagaaac gagatgactt cgaaaagctg | 480 | |
| actaattatt cggtaactga cttgaatgtc aacgcaaaag caatacatga actcatccaa | 540 | |
| gtgatggctg aactgtcgcc agcagctaaa acagggaagc gaaaaaggag tcagatgctg | 600 | |
| tttcgaggtc gaagagcatc ccagtaatgg ttgtcctgcc tgcaatattt gaattttaaa | 660 | |
| tctaaatcta tttattaata tttaacatta tttatatggg gaatatattt ttagactcat | 720 | |
| caatcaaata agtatttata atagcaactt ttgtgtaatg aaaatgaata tctattaata | 780 | |
| tatgtattat ttataattcc tatatcctgt gactgtctca cttaatcctt tgttttctga | 840 | |
| ctaattaggc aaggctatgt gattacaagg ctttatctca ggggccaact aggcagccaa | 900 | |
| cctaagcaag atcccatggg ttgtgtgttt atttcacttg atgatacaat gaacacttat | 960 | |
| aagtgaagtg atactatcca gttactgccg gtttgaaaat atgcctgcaa tctgagccag | 1020 | |
| tgctttaatg gcatgtcaga cagaacttga atgtgtcagg tgaccctgat gaaaacatag | 1080 | |
| catctcagga gatttcatgc ctggtgcttc caaatattgt tgacaactgt gactgtaccc | 1140 | |
| aaatggaaag taactcattt gttaaaatta tcaatatcta atatatatga ataaagtgta | 1200 | |
| agttcacaac aaaaaaaaaa aaaaaaaaaa aaaaaaaaa | 1240 | |

<210> SEQ ID NO 3
<211> LENGTH: 1201
<212> TYPE: DNA
<213> ORGANISM: Homo sapiens

<400> SEQUENCE: 3

| | | |
|---|---|---|
| aatattagag tctcaacccc caataaatat aggactggag atgtctgagg ctcattctgc | 60 | |
| cctcgagccc accgggaacg aaagagaagc tctatctccc ctccaggagc ccagctatga | 120 | |
| actccttctc cacaagcgcc ttcggtccag ttgccttctc cctggggctg ctcctggtgt | 180 | |
| tgcctgctgc cttccctgcc ccagtacccc caggagaaga ttccaaagat gtagccgccc | 240 | |
| cacacagaca gccactcacc tcttcagaac gaattgacaa acaaattcgg tacatcctcg | 300 | |

-continued

| | |
|---|---|
| acggcatctc agccctgaga aaggagacat gtaacaagag taacatgtgt gaaagcagca | 360 |
| aagaggcact ggcagaaaac aacctgaacc ttccaaagat ggctgaaaaa gatggatgct | 420 |
| tccaatctgg attcaatgag gagacttgcc tggtgaaaat catcactggt cttttggagt | 480 |
| ttgaggtata cctagagtac ctccagaaca gatttgagag tagtgaggaa caagccagag | 540 |
| ctgtgcagat gagtacaaaa gtcctgatcc agttcctgca gaaaaaggca agaatctag | 600 |
| atgcaataac caccctgac ccaaccacaa atgccagcct gctgacgaag ctgcaggcac | 660 |
| agaaccagtg gctgcaggac atgacaactc atctcattct gcgcagcttt aaggagttcc | 720 |
| tgcagtccag cctgagggct cttcggcaaa tgtagcatgg gcacctcaga ttgttgttgt | 780 |
| taatgggcat tccttcttct ggtcagaaac ctgtccactg gcacagaac ttatgttgtt | 840 |
| ctctatggag aactaaaagt atgagcgtta ggacactatt ttaattattt ttaatttatt | 900 |
| aatatttaaa tatgtgaagc tgagttaatt tatgtaagtc atatttatat ttttaagaag | 960 |
| taccacttga acattttat gtattagttt tgaaataata atggaaagtg gctatgcagt | 1020 |
| ttgaatatcc tttgtttcag agccagatca tttcttggaa agtgtaggct tacctcaaat | 1080 |
| aaaatggctaa cttatacata ttttaaaga aatatttata ttgtatttat ataatgtata | 1140 |
| aatggttttt ataccaataa atggcatttt aaaaaattca gcaaaaaaa aaaaaaaaa | 1200 |
| a | 1201 |

<210> SEQ ID NO 4
<211> LENGTH: 1859
<212> TYPE: DNA
<213> ORGANISM: Homoo sapiens

<400> SEQUENCE: 4

| | |
|---|---|
| gcaggcacaa actcatccat ccccagttga ttggaagaaa caacgatgac tcctgggaag | 60 |
| acctcattgg tgtcactgct actgctgctg agcctggagg ccatagtgaa ggcaggaatc | 120 |
| acaatcccac gaaatccagg atgcccaaat tctgaggaca agaacttccc ccggactgtg | 180 |
| atggtcaacc tgaacatcca taaccggaat accaatacca atcccaaaag gtcctcagat | 240 |
| tactacaacc gatccaccct accttggaat ctccaccgca atgaggaccc tgagagatat | 300 |
| ccctctgtga tctgggaggc aaagtgccgc cacttgggct gcatcaacgc tgatgggaac | 360 |
| gtggactacc acatgaactc tgtccccatc cagcaagaga tcctggtcct gcgcagggag | 420 |
| cctccacact gccccaactc cttccggctg gagaagatac tggtgtccgt gggctgcacc | 480 |
| tgtgtcaccc cgattgtcca ccatgtggcc taagagctct ggggagccca cactccccaa | 540 |
| agcagttaga ctatggagag ccgacccagc ccctcaggaa ccctcatcct tcaaagacag | 600 |
| cctcatttcg gactaaactc attagagttc ttaaggcagt ttgtccaatt aaagcttcag | 660 |
| aggtaacact tggccaagat atgagatctg aattaccttt ccctctttcc aagaaggaag | 720 |
| gtttgactga gtaccaattt gcttcttgtt tactttttta agggctttaa gttatttatg | 780 |
| tatttaatat gccctgagat aactttgggg tataagattc catttaatg aattacctac | 840 |
| tttattttgt ttgtctttt aaagaagata agattctggg cttggaatt ttattattta | 900 |
| aaaggtaaaa cctgtatttta tttgagctat ttaaggatct atttatgttt aagtatttag | 960 |
| aaaaaggtga aaaagcacta ttatcagttc tgcctaggta aatgtaagat agaattaaat | 1020 |
| ggcagtgcaa aatttctgag tctttacaac atacggatat agtatttcct cctctttgtt | 1080 |
| tttaaaagtt ataacatggc tgaaaagaaa gattaaacct actttcatat gtattaattt | 1140 |

```
aaatttttgca  atttgttgag   gttttacaag   agatacagca   agtctaactc   tctgttccat    1200
taaaccctta   taataaaatc   cttctgtaat   aataaagttt   caaaagaaaa   tgtttatttg    1260
ttctcattaa   atgtatttta   gcaaactcag   ctcttcccta   ttgggaagag   ttatgcaaat    1320
tctcctataa   gcaaaacaaa   gcatgtcttt   gagtaacaat   gacctggaaa   tacccaaaat    1380
tccaagttct   cgatttcaca   tgccttcaag   actgaacacc   gactaaggtt   ttcatactat    1440
tagccaatgc   tgtagacaga   agcattttga   taggaataga   gcaaataaga   taatggccct    1500
gaggaatggc   atgtcattat   taaagatcat   atggggaaaa   tgaaaccctc   cccaaaatac    1560
aagaagttct   gggaggagac   attgtcttca   gactacaatg   tccagtttct   ccccctagact    1620 caggcttcct   ttggagatta   aggcccctca   gagatcaaca   gaccaacatt   tttctcttcc    1680
tcaagcaaca   ctcctagggc   ctggcttctg   tctgatcaag   gcaccacaca   acccagaaag    1740
gagctgatgg   ggcagaacga   actttaagta   tgagaaaagt   tcagcccaag   taaaataaaa    1800
actcaatcac   attcaattcc   agagtagttt   caagtttcac   atcgtaacca   ttttcgccc     1859
```

<210> SEQ ID NO 5
<211> LENGTH: 269
<212> TYPE: PRT
<213> ORGANISM: Homo sapiens

<400> SEQUENCE: 5

```
Met Ala Glu Val Pro Glu Leu Ala Ser Glu Met Met Ala Tyr Tyr Ser
1               5                   10                  15

Gly Asn Glu Asp Asp Leu Phe Phe Glu Ala Asp Gly Pro Lys Gln Met
                20                  25                  30

Lys Cys Ser Phe Gln Asp Leu Asp Leu Cys Pro Leu Asp Gly Gly Ile
            35                  40                  45

Gln Leu Arg Ile Ser Asp His His Tyr Ser Lys Gly Phe Arg Gln Ala
        50                  55                  60

Ala Ser Val Val Val Ala Met Asp Lys Leu Arg Lys Met Leu Val Pro
65                  70                  75                  80

Cys Pro Gln Thr Phe Gln Glu Asn Asp Leu Ser Thr Phe Phe Pro Phe
                85                  90                  95

Ile Phe Glu Glu Glu Pro Ile Phe Phe Asp Thr Trp Asp Asn Glu Ala
                100                 105                 110

Tyr Val His Asp Ala Pro Val Arg Ser Leu Asn Cys Thr Leu Arg Asp
            115                 120                 125

Ser Gln Gln Lys Ser Leu Val Met Ser Gly Pro Tyr Glu Leu Lys Ala
        130                 135                 140

Leu His Leu Gln Gly Gln Asp Met Glu Gln Gln Val Val Phe Ser Met
145                 150                 155                 160

Ser Phe Val Gln Gly Glu Glu Ser Asn Asp Lys Ile Pro Val Ala Leu
                165                 170                 175

Gly Leu Lys Glu Lys Asn Leu Tyr Leu Ser Cys Val Leu Lys Asp Asp
                180                 185                 190

Lys Pro Thr Leu Gln Leu Glu Ser Val Asp Pro Lys Asn Tyr Pro Lys
            195                 200                 205

Lys Lys Met Glu Lys Arg Phe Val Phe Asn Lys Ile Glu Ile Asn Asn
        210                 215                 220

Lys Leu Glu Phe Glu Ser Ala Gln Phe Pro Asn Trp Tyr Ile Ser Thr
225                 230                 235                 240

Ser Gln Ala Glu Asn Met Pro Val Phe Leu Gly Gly Thr Lys Gly Gly
                245                 250                 255
```

-continued

```
Gln Asp Ile Thr Asp Phe Thr Met Gln Phe Val Ser Ser
            260                 265

<210> SEQ ID NO 6
<211> LENGTH: 166
<212> TYPE: PRT
<213> ORGANISM: Homo sapiens

<400> SEQUENCE: 6

Met Lys Tyr Thr Ser Tyr Ile Leu Ala Phe Gln Leu Cys Ile Val Leu
1               5                   10                  15

Gly Ser Leu Gly Cys Tyr Cys Gln Asp Pro Tyr Val Lys Glu Ala Glu
            20                  25                  30

Asn Leu Lys Lys Tyr Phe Asn Ala Gly His Ser Asp Val Ala Asp Asn
        35                  40                  45

Gly Thr Leu Phe Leu Gly Ile Leu Lys Asn Trp Lys Glu Glu Ser Asp
    50                  55                  60

Arg Lys Ile Met Gln Ser Gln Ile Val Ser Phe Tyr Phe Lys Leu Phe
65                  70                  75                  80

Lys Asn Phe Lys Asp Asp Gln Ser Ile Gln Lys Ser Val Glu Thr Ile
                85                  90                  95

Lys Glu Asp Met Asn Val Lys Phe Phe Asn Ser Asn Lys Lys Lys Arg
            100                 105                 110

Asp Asp Phe Glu Lys Leu Thr Asn Tyr Ser Val Thr Asp Leu Asn Val
        115                 120                 125

Gln Arg Lys Ala Ile His Glu Leu Ile Gln Val Met Ala Glu Leu Ser
    130                 135                 140

Pro Ala Ala Lys Thr Gly Lys Arg Lys Arg Ser Gln Met Leu Phe Arg
145                 150                 155                 160

Gly Arg Arg Ala Ser Gln
                165

<210> SEQ ID NO 7
<211> LENGTH: 212
<212> TYPE: PRT
<213> ORGANISM: Homo sapiens

<400> SEQUENCE: 7

Met Asn Ser Phe Ser Thr Ser Ala Phe Gly Pro Val Ala Phe Ser Leu
1               5                   10                  15

Gly Leu Leu Leu Val Leu Pro Ala Ala Phe Pro Ala Pro Val Pro Pro
            20                  25                  30

Gly Glu Asp Ser Lys Asp Val Ala Ala Pro His Arg Gln Pro Leu Thr
        35                  40                  45

Ser Ser Glu Arg Ile Asp Lys Gln Ile Arg Tyr Ile Leu Asp Gly Ile
    50                  55                  60

Ser Ala Leu Arg Lys Glu Thr Cys Asn Lys Ser Asn Met Cys Glu Ser
65                  70                  75                  80

Ser Lys Glu Ala Leu Ala Glu Asn Asn Leu Asn Leu Pro Lys Met Ala
                85                  90                  95

Glu Lys Asp Gly Cys Phe Gln Ser Gly Phe Asn Glu Glu Thr Cys Leu
            100                 105                 110

Val Lys Ile Ile Thr Gly Leu Leu Glu Phe Glu Val Tyr Leu Glu Tyr
        115                 120                 125
```

-continued

Leu Gln Asn Arg Phe Glu Ser Glu Glu Ala Arg Ala Val Gln
    130                 135                 140

Met Ser Thr Lys Val Leu Ile Gln Phe Leu Gln Lys Ala Lys Asn
145                 150                 155                 160

Leu Asp Ala Ile Thr Thr Pro Asp Pro Thr Thr Asn Ala Ser Leu Leu
                165                 170                 175

Thr Lys Leu Gln Ala Gln Asn Gln Trp Leu Gln Asp Met Thr Thr His
                180                 185                 190

Leu Ile Leu Arg Ser Phe Lys Glu Phe Leu Gln Ser Ser Leu Arg Ala
            195                 200                 205

Leu Arg Gln Met
    210

<210> SEQ ID NO 8
<211> LENGTH: 155
<212> TYPE: PRT
<213> ORGANISM: Homo sapiens

<400> SEQUENCE: 8

Met Thr Pro Gly Lys Thr Ser Leu Val Ser Leu Leu Leu Leu Leu Ser
1               5                   10                  15

Leu Glu Ala Ile Val Lys Ala Gly Ile Thr Ile Pro Arg Asn Pro Gly
                20                  25                  30

Cys Pro Asn Ser Glu Asp Lys Asn Phe Pro Arg Thr Val Met Val Asn
            35                  40                  45

Leu Asn Ile His Asn Arg Asn Thr Asn Thr Asn Pro Lys Arg Ser Ser
        50                  55                  60

Asp Tyr Tyr Asn Arg Ser Thr Ser Pro Trp Asn Leu His Arg Asn Glu
65                  70                  75                  80

Asp Pro Glu Arg Tyr Pro Ser Val Ile Trp Glu Ala Lys Cys Arg His
                85                  90                  95

Leu Gly Cys Ile Asn Ala Asp Gly Asn Val Asp Tyr His Met Asn Ser
                100                 105                 110

Val Pro Ile Gln Gln Glu Ile Leu Val Leu Arg Arg Glu Pro Pro His
            115                 120                 125

Cys Pro Asn Ser Phe Arg Leu Glu Lys Ile Leu Val Ser Val Gly Cys
        130                 135                 140

Thr Cys Val Thr Pro Ile Val His His Val Ala
145                 150                 155

<210> SEQ ID NO 9
<211> LENGTH: 21
<212> TYPE: DNA
<213> ORGANISM: Artificial
<220> FEATURE:
<223> OTHER INFORMATION: primer

<400> SEQUENCE: 9
cagctacgaa tctccgacca c                                                 21

<210> SEQ ID NO 10
<211> LENGTH: 20
<212> TYPE: PRT
<213> ORGANISM: Artificial
<220> FEATURE:
<223> OTHER INFORMATION: primer

```
<400> SEQUENCE: 10

Gly Gly Cys Ala Gly Gly Gly Ala Ala Cys Cys Ala Gly Cys Ala Thr
1               5                   10                  15

Cys Thr Thr Cys
            20
```